United States Patent [19]

Bridge et al.

[11] Patent Number: 5,189,022

[45] Date of Patent: * Feb. 23, 1993

[54] COMPOSITION FOR THE TREATMENT OF CHRONIC FATIGUE SYNDROME

[75] Inventors: Thomas P. Bridge, Washington, D.C.; Frederick K. Goodwin, Chevy Chase, Md.

[73] Assignee: The United States of America as represented by the Secretary of Health and Human Services, Washington, D.C.

[*] Notice: The portion of the term of this patent subsequent to Nov. 5, 2008 has been disclaimed.

[21] Appl. No.: 696,556

[22] Filed: May 8, 1991

Related U.S. Application Data

[63] Continuation-in-part of Ser. No. 352,313, May 16, 1989, Pat. No. 5,063,206, which is a continuation-in-part of Ser. No. 285,559, Dec. 16, 1988, abandoned, which is a continuation-in-part of Ser. No. 199,873, May 27, 1988, abandoned.

[51] Int. Cl.$^5$ ............................................ A61K 37/02
[52] U.S. Cl. ........................................ 514/16; 514/15
[58] Field of Search ..................................... 514/15, 16

[56] References Cited

U.S. PATENT DOCUMENTS 4,880,626 11/1989 McMichael ........................... 424/88
5,013,739 5/1991 Bihari et al. ........................ 514/282

OTHER PUBLICATIONS

Jordan Grafman, et al. Cognitive and Mood-State Changes in Patients with Chronic Fatigue Syndrome. vol. 13 Jan.-Feb. 1991.
James T. Becker, Methodologic Considerations in Assessment of Cognitive Function in Chronic Fatigue Syndrome vol. 13 Jan.-Feb. 1991.
Straus-Stephen-E. et al., Acyclovir Treatment of The Chronic Fatigue Syndrome: Lack of Efficacy in a Placebo-Controlled Trial.
Lloyd-Andrew et al., A Double-Blind, Placebo-Controlled Trial of Intravenous Immunoglobulin Therapy in Patients with Chronic Fatigue Syndrome. The American Journal of Medicine, Nov. 1990 89(5), pp. 561–568.
Peterson-Phillip-K. et al., A Controlled Trial of Intravenous Immunoglobulin G in Chronic Fatigue Syndrome. The American Journal of Medicine. 1990 No. 89 (5). pp. 554–560.
Linde, R. et al., Sixth Int'l Conference of AIDS, vol. 75 1-3, Abs. 2183, 1990.

Primary Examiner—Merrell C. Cashion, Jr.
Assistant Examiner—Susan M. Perkins
Attorney, Agent, or Firm—Cushman, Darby and Cushman

[57] ABSTRACT

The present invention relates to a method of treating chronic fatigue syndrome not associated with an HIV infection. In the method of the present invention patients are administered a pharmaceutically acceptable carrier together with (1) a neuropsychiatrically effective amount of a linear peptide of formula (I):

$$R^a\text{-Ser-Thr-Thr-Thr-Asn-Tyr-}R^6 \qquad (I)$$

wherein
$R^a$ is Ala, D-Ala or Cys-Ala-, and
$R^6$ is Thr, Thr-amide, Thr-Cys or Thr-Cys-amide, or a derivative of the peptide or a physiologically acceptable salt thereof; or (2) a neuropsychiatrically effective amount of a linear peptide of formula (II):

$$R^1\text{-}R^2\text{-}R^3\text{-}R^4\text{-}R^5 \qquad (II)$$

wherein
$R^1$ is X-Y or Y when Y is Thr-, Ser-, Asn-, Leu-, Ile-, Arg- or Glu-, and X is Cys;
$R^2$ is Thr-, Ser- or Asp;
$R^3$ is Thr, Ser, Asn, Arg, Gln, Lys or Trp;
$R^4$ is Tyr; and
$R^5$ is Z-X or Z wherein Z is any amino acid and X is Cys, or a derivative of the peptide or a physiologically acceptable salt thereof; or (e) a neuropsychiatrically effective amount of a linear peptide of formula (III):

$$R^x\text{-}R^2\text{-}R^3\text{-}R^4\text{-}R^y \qquad (III)$$

wherein
$R^x$ is Ala-$R^1$, D-Ala-$R^1$ or X-Ala-$R^1$ wherein X, $R^1$, $R^2$, $R^3$, $R^4$ are as defined above, and $R^y$ is Thr-, Thr-amide or Thr-Cys, or a derivative of the peptide or a physiologically acceptable salt thereof.

5 Claims, No Drawings

COMPOSITION FOR THE TREATMENT OF CHRONIC FATIGUE SYNDROME

The present application is a continuation-in-part of the Bridge et al application Ser. No. 07/352,313 filed May 16, 1989 now U.S. Pat. No. 5,063,206, which is a continuation-in-part of application Ser. No. 07/285,559 filed Dec. 16, 1988 now abandoned, which is a continuation-in-part of application Ser. No. 07/199,873 filed May 27, 1988 now abandoned. The entire contents of above applications are hereby incorporated by reference.

BACKGROUND OF THE INVENTION

The chronic fatigue syndrome (CFS) has been recognized as an illness characterized by easy fatigability, prolonged lassitude and disturbances of sleep, sometimes but not always appearing to follow symptoms of an acute viral illness [Holmes et al, Ann Intern Med 108(3), 387-389 (1988) and Buchwald et al, JAMA 257(17), 2303-2307 (1987)]. Originally thought to be due to chronic Epstein Barr virus infection, this cause of CFS has been largely discredited [Koo, D., West J Med 150(50), 590-596 (1989)].

Recent observations indicate that one of the most prominent features of this syndrome is cognitive impairment. Although this impairment has been reported by patients and verified anecdotally by their physicians, it has not been quantified. No national survey of the frequency of the disease has been performed, but one report indicated the syndrome was common in general medicine practices [Buchwald et al, JAMA 257(17), 2303-2307 (1987)].

Peptide T has been shown to be associated with significant improvement in measurable cognitive function of persons with human immunodeficiency virus (HIV) [Bridge et al, Lancet II (8656), 226 (1989)].

In recent work, protein kinase A activity in humans has been shown to be increased by Peptide T. This enzyme system subserves the activity of the cyclic AMP system, the second order messenger system for a number of central nervous system functions including memory and circadian rhythmicity. Reductions in activity of this enzyme have been observed in chronic fatigue syndrome patients, and Peptide T increases pka activity in the same in vitro tests. These observations suggest that the effects of Peptide T seen in earlier HIV studies are related more generally to virally infected persons, and not restricted to HIV infections alone.

SUMMARY OF THE INVENTION

It is an object of the present invention to provide a treatment for Chronic Fatigue Syndrome.

In one embodiment, the present invention relates to a method of treating chronic fatigue syndrome not associated with an HIV infection. The method comprises administering to a patient with chronic fatigue syndrome a pharmaceutically acceptable carrier with (1) a neuropsychiatrically effective amount of a linear peptide of formula (I):

$$R^a\text{-Ser-Thr-Thr-Thr-Asn-Tyr-}R^b \tag{I}$$

wherein $R^a$ is Ala, D-Ala or Cys-Ala-, and $R^b$ is Thr, Thr-amide, Thr-Cys or Thr-Cys-amide, or a derivative of peptide I or a physiologically acceptable salt thereof; or (2) a neuropsychiatrically effective amount of a linear peptide of formula (II):

$$R^1\text{-}R^2\text{-}R^3\text{ }R^4\text{-}R^5 \tag{II}$$

wherein $R^1$ is X-Y or Y when Y is Thr-, Ser-, Asn-, Leu-, Ile-, Arg- or Glu-, and X is Cys;

$R^2$ is Thr-, Ser- or Asp;

$R^3$ is Thr, Ser, Asn, Arg, Gln, Lys or Trp;

$R^4$ is Tyr; and $R^5$ is Z-X or Z wherein Z is any amino acid and X is Cys, or a derivative of peptide II or a physiologically acceptable salt thereof, or (3) a neuropsychiatrically effective amount of a linear peptide of formula (III):

$$R^x\text{-}R^2\text{-}R^3R^4\text{-}R^y \tag{III}$$

wherein $R^x$ is Ala-$R^1$, D-Ala-$R^1$ or X-Ala-$R^1$ wherein X, $R^1$, $R^2$, $R^3$, $R^4$ are as defined above, and $R^y$ is Thr-, Thr-amide or Thr-Cys, or a derivative of peptide III or a physiologically acceptable salt thereof.

Various other objects and advantages of the present will be apparent from the following description of the invention.

DETAILED DESCRIPTION OF THE INVENTION

The present invention relates to methods of treating CFS not associated with an HIV infection. The present inventors have discovered a class of peptides which when administered to patients not infected with HIV but having CFS reduce fatigue, tension, anger, confusion and improve cognitive and neuromotor performance. The method of the present invention comprises administering to a patient without an HIV infection a neuropsychiatrically effective amount of a peptide described herein together with a pharmaceutically acceptable carrier.

There are three groups of linear peptides suitable for use in the method of the present invention. The first group comprises linear peptides of formula (I):

$$R^a\text{Ser-Thr-Thr-Thr-Asn-Tyr-}R^b \tag{I}$$

wherein $R^a$ is Ala, D-Ala or Cys-Ala-, and $R^b$ is Thr, Thr-amide, Thr-Cys or Thr-Cys-amide; or a derivative thereof, for example, an ester or amide derivative.

Preferred peptides of formula (I) include, Peptide T, D-Ala-Ser-Thr-Thr-Thr-Asn-Tyr-Thr and D-Ala-Ser-Thr-Thr-Thr-Asn-Tyr-Thr-amide.

The second group comprises linear peptides of formula (II):

$$R^1\text{-}R^2\text{-}r^3R^4\text{-}R^5 \tag{II}$$

wherein $R^2$ is Thr-, Ser-, Asn-, Leu-, Ile-, Arg-, Glu-, Cys-Thr, Cys-Ser-, Cys-Asn-, Cys-Leu-, Cys-Ile-, Cys-Arg-, or Cys-Glu-;

$R^2$ is Thr, Ser or Asp;

$R^3$ is Thr, Ser, Asn, Arg, Gln, Lys or Trp;

$R^4$ is Tyr; and $R^5$ is Z-X or Z wherein Z is any naturally occurring amino acid (preferably Thr, Arg or Gly) and X is Cys.

Preferred peptides of formula (II) include Thr-Asp-Asn-Tyr-Thr, Thr-Thr-Ser-Tyr-Thr, Thr-Thr-Asn-Tyr-Thr, their D-analogues (that this, D-Thr at the amino terminal) and/or analogues with an amide derivative at the carboxy terminal.

The $R^5$ position is not critical as the amino acid occupying the position does not affect the activity of the peptide. Any substituted or unsubstituted naturally occurring amino acid can be used in this position. In fact, the $R^5$ position can be left empty.

The third group comprises linear peptides of formula (III):

$$R^x\text{-}R^2\text{-}R^3R^4\text{-}R^y \qquad (III)$$

wherein $R^x$ is Ala-$R^1$, D-Ala-$R^1$ or X-Ala-$R^1$ wherein X, $R^1$, $R^2$, $R^3$, $R^4$ are as defined above and $R^y$ is Thr-, Thr-amide or Thr-Cys; or derivatives thereof, such as ester and amide derivatives.

In addition to the three groups of peptides, physiologically acceptable salts of the peptides can be used.

The peptides of the present invention may be modified by known methods to enhance passage of molecules across the blood-brain barrier. Acetylation has proven to be especially useful for enhancing binding activity of the peptides. The terminal amino and carboxy sites are particularly preferred sites for modification. In addition, the peptides may be modified to provide improved stability and oral availability, such as, by altering a constraining conformation. For example, the addition of D-Ala or the use of the amide form of the peptide increases the stability of the peptide.

The peptides of the present invention can be produced using a number of known techniques. For example, the peptides can be custom synthesized or isolated from the virus using known methods. Peptides can also be produced using solid phase and liquid phase methods.

For example, the solid phase method of Merrifield U.S. Pat. No. 3,531,258 can be used. In this process, the peptide is synthesized in a stepwise manner while the carboxy end of the chain is covalently attached to the insoluble support. During the intermediate synthetic stages the peptide remains on the solid support and therefore can be conveniently manipulated. The solid support can be chloromethylated styrene-divinylbenzene copolymer.

An n-protected form of the carboxy terminal amino acid, e.g. a t-butoxycarbonyl protected (Boc-) amino acid, is reacted with the chloromethyl residue of the chloromethylated styrene divinylbenzene copolymer resin to produce a protected amino acyl derivative of the resin, where the amino acid is coupled to the resin as a benzyl ester. This is deprotected and reacted with a protected form of the next required amino acid thus producing a protected dipeptide attached to the resin. The amino acid will generally be used in its activated form, e.g., by use of a carbodiimide or active ester. This sequence of steps is repeated causing the peptide chain to grow one residue at a time by condensation at the amino end with the required N-protected amino acid until the required peptide has been assembled on the resin. The peptide-resin is then treated with anhydrous hydrofluoric acid to cleave the ester linkage to the resin, in order to liberate the required peptide. Side chain functional groups of amino acids which must be blocked during the synthetic procedure using conventional methods, may also be simultaneously removed. Synthesis of a peptide with an amide group on its carboxy terminal can be carried out in any conventional manner, for example, using a 4-methylbenzhydrlamine resin.

Synthesized peptides are preferred as they are free of viral and cellular debris. Thus, undesired reactions to contaminants does not occur when synthesized peptides are used.

The peptides of the present invention can be prepared as pharmaceutical compositions containing pharmaceutically acceptable carriers or excipients. Other active ingredients, such as antimicrobial agents and preservatives may also be included in the compositions. The peptides can be prepared as compositions for nasal, buccal, parenteral, topical or rectal administration. The composition can be in the form of a cyclodextrin inclusion complex or a lyophilized powder.

The peptides of the present invention can be administered via intranasal or intravenous routes. Preferably, the peptides are administered via intranasal. The treatment given a patient will depend on several factors including the route of administration and the condition of the patient. These factors are easily assessed by the attending physician and the appropriate treatment determined therefrom.

For administration by injection or infusion, the daily dosage for an adult human of approximately 70 kg body weight will preferably range from 0.01 mg to 10 mg per day, more preferably 0.1 mg to 2 mg per day, which may be administered in 1 to 4 doses, for example, depending on the route of administration and the condition of the patient. For administration nasally or sublingually a somewhat higher dosage is desirable. An adult human of about 70 kg body weight will preferably be given 0.2 to 30 mg per day, more preferably 1.2 mg to 60 mg per day. Preferably compositions of the present invention are administered intranasally as a spray.

The following non-limiting examples are given to further describe the present invention and are not deemed limitative thereof.

EXAMPLES

Peptide T Ala-Ser-Thr-Thr-Thr-Asn-Tyr-Thr was given intranasally to five patients meeting diagnostic criteria of Chronic Fatigue Syndrome. That is, the patients between the age of 18 and 60, demonstrating at least a 1 S.D. impairment of two cognitive function domains (e.g., memory, visuo-spatial etc) or a 2 S.D. impairment in one domain after three sequences of the repeatable tests described below, having a human herpes virus (HHV) PCR signal equal to or greater than 1.5 S.D. above the control mean, having a Karnofsky performance status of less than 80%, having a fatigue score of >50 and having a vigor score of <50 on the profile of mood state (POMS) test.

Prior to the start of treatment, the patients were given physical examination including vital signs (supine blood pressure, heart rate, temperature and respiratory rate), and height and weight determination. Laboratory tests were conducted to determine CBC with differential and platelet count and blood chemistry including tests of liver function, urinalysis and HIV antibody by ELISA. Skin tests (Merieux Multitest) for delayed hypersensitivity were also given.

Patients pre-treatment laboratory results equaled or exceeded the following values: WBC>2000/mm³, Hg>10 G/dl, platelets>75,000/mm³, Prothrombin time>90% control, Creatinine<1.5 mg/dl, SGOT<3x normal, bilirubin<2.0.

The patients were also given a neuropsychologic test battery including the Beck test [Beck et al, Beck Depression Inventory. San Diego, Psychological Corp., 1987], the Grooved Pegboard, Trails B test [Bornstein, RA., J Clin Psychol 41, 398–408 (1985)], the PASAT test [Gronwall, DMA., Perc Motor Skills 44, 367–373 (1977)], the Stroop test [Jensen et al, Acta Psychologica 25, 36–39 (1966)], the POMS test [McNair et al, EDITS Manual for the Profile of Mood States (POMS). San Diego, Educational and Industrial Testing Service, 1971] and the Karnofsky test [Karnofsky et al, Cancer 1, 634–656 (1948)].

Each impaired patient was seropositive for Human Herpes Virus 6 (HHV-6) but negative for Human Immunodeficiency Virus I (HIV-1). Treatment lasted 12 weeks, during which time the patients received either 5 or 10 mg Peptide T as intranasal preparation three times per day for 8 weeks. The patients were blind to the drug dosage and drug condition. The dosages were assigned randomly. In addition, blinded randomization was used to assign patients to either the group beginning treatment with Peptide T for eight weeks followed by four weeks for placebo or the group beginning treatment with four weeks of placebo followed by eight weeks of Peptide T.

The patients were evaluated both by symptom report forms and by neuropsychologic evaluation.

Preparations were made by mixing 1200 ml 2.5% mannitol and 3.56 grams of a Peptide T preparation containing 91.7% peptide. The mixture was adjusted to pH 6.15. The solution was filtered through a 0.22 micron Durapor® filter and the sterilized solution was delivered by a peristaltic pump in 2 ml aliquots into sterile 5 ml serum vials. The vials were stoppered and transferred to the freeze drier. After drying was accomplished, the vials were sealed and stored under freezing conditions for up to several months.

Alternatively, the composition was prepared by adding distilled water (768 ml) to 9.9 grams of Peptide T supplied by Peninsula which contained 85% peptide. The powdered peptide product was very light and very static. The solution was then transferred to a silo filtering apparatus and filtered through a 0.22 micron Durapor® filter membrane into a sterile receptacle. The sterile solution was dispensed into vials and dried in the manner previously described.

The first observation to be confirmed was that there was no evidence of drug-related toxicity present in these patients. By study criteria, basic laboratory values for blood chemistry and hematologic profiles were essentially normative at baseline, therefore it is not possible to comment as to whether Peptide T treatment was associated with any improvement in these parameters in Chronic Fatigue Syndrome.

NEUROPSYCHOLOGIC

By diagnostic criteria, all patients admitted to the study had cognitive impairments of at least one S.D. below norm on two separate tests in the neuropsychologic battery prior to drug testing. The tests used in this battery are as follows (including domains and localized areas tested):

| LOCALIZATION OF NEUROPSYCHOLOGIC FUNCTION | | |
|---|---|---|
| REGION | DOMAIN | TEST |
| POST. FRONTAL | MOTOR | GROOVED PEGBOARD (GPB-N) |
| PRE-FRONTAL/PARIETAL | EXECUTIVE/ATTENTION | TRAILMAKING TEST (TMT) STROOP COLOR WORD |
| HIPPOCAMPUS/AMYGDALA SUBCORTICAL/TEMPORAL | MEMORY | REPEAT VERBAL LEARNING TEST (RVLT) |
| FRONTAL | CALCULATION/SET SHIFT | PACED AUDITORY SERIAL ADDITION TEST (PASAT) |

Under consideration are 20 tests (5 tests/patient×4 patients), of which twelve tests were at least 1 S.D. below norm at baseline. Of these 12 abnormal tests, 10 test results had normalized by the end of the study. Shown below are both the sample mean test results from each test in the battery and for the battery overall.

| MEAN NEUROPSYCHOLOGIC TEST SCORE RESULTS IN POPULATION NORM S.D. | | | | |
|---|---|---|---|---|
| TEST | BASELINE | POST-TRAINING | PLACEBO | END OF RX |
| PASAT | −.6 | −.5 | .5 | .8 |
| STROOP | −1.4 | −.1 | −.1 | 1.2 |
| TMB | −.8 | −.1 | −.1 | .6 |
| RVLT | −1.0 | −1.8 | −1.8 | −.9 |
| GPB-N | −1.1 | −.7 | −.3 | .1 |
| OVERALL MEAN | −1.0 | −.6 | −.4 | .4 |

With regard to the above table, "baseline" is the first neuropsychologic testing session and "post-training" is the third repeat session of cognitive neuromotor testing before drug initiation. This series of three testing sessions minimizes learning effects. "Placebo" was tested after the completion of the placebo phase, which is the first four weeks of the study. "End of rx" is the final testing session prior to cessation of drug testing. The numbers shown are average standard deviations below or above appropriate population norms on these tests, controlling for age, sex, and educational attainment. Individually, these subjects demonstrated a normalization of test results when neuropsychologic testing was abnormal at baseline (p<0.005, two tailed, Fisher Exact test)

Moreover, they demonstrate an overall improvement in neuropsychologic function of 1 S.D. on average compared to post-training sessions, which is considered clinically significant. There was an approximate 0.8 S.D. improvement in function compared to placebo on these tests, which the inventors estimate would achieve conventionally accepted levels of statistical significance in a sample of approximately 30–40 subjects.

SYMPTOM REPORT

The relevant symptom reports here include the Profile of Mood States (POMS), Fatigue and Vigor subscales; the Beck Depression Inventory, the Subjective Memory Questionnaire (SMQ), and the Karnosfsky Performance Scale (KPS). The data from this sample are tabulated below:

CHANGES IN SYMPTOM REPORT SCORES IN PEPTIDE T PATIENTS

| TEST | BASELINE | PLACEBO | END OF DRUG |
|---|---|---|---|
| Beck | 12.0 | 9.3 | 9.0 |
| SMQ | −42.5 | −26.8 | −19.8 |
| POMS Fatigue | 61 | 58 | 46 |
| Vigor | 42 | 47 | 52 |
| KFS | 68 | 72 | 82 |

With regard to the above data, it should be noted that these are self report scales, except for the KFS, which is observer rated. In all cases, however, no learning effects are expected, and hence comparisons are not needed to a post-training point.

Scores for the POMS scale are reported in T scores, every 10 points representing a one SD change. For Vigor, increases represent improvement; the converse is true for Fatigue. The above reported changes in the Beck Depression Inventory show clinically non-significant changes. Clinically significant scores on the Beck Depression Inventory are scores greater than 24. The SMQ has not been standardized to population norms.

It can be said that these subjects reported considerable symptomatology with memory function, which improves both with placebo and active drug (score range: −48 to +48; low scores represent extreme reported disability). There was a one SD decrease in fatigue scores compared to placebo scores, and a 0.5 SD increase in vigor scores reported. The changes in Fatigue scores are clinically significant. With regard to KFS scores, it is noteworthy that, on average, the patient group went from being evaluated as being able to care for self, but unable to carry on normal activity or work, to being able to accomplish normal activity with effort and having some signs or symptoms of disease.

IMMUNOLOGIC

The principal immunologic test in this study was the PCR signal for HHV-6. There was no diminution of this signal on testing post drug in these patients. Hence, the improvements observed are not likely to be associated with any direct anti-viral activity of this drug.

MECHANISM OF ACTION

Recent data have become available on these subjects and on normal controls receiving Peptide T that suggest that Peptide T exerts its symptomatic effects through the cyclic AMP (c-AMP) system, specifically on the R1 and R2 types of protein kinase A (pkA). This system is a second order messenger system that modified many neurotransmitter system functions. In samples from these subjects, Peptide T showed considerable increase (up to 6 fold) in pkA activity during on drug periods compared to baseline conditions. This effect is magnified in in vitro testing when cyclic AMP analogues are present to increase the metabolic substrate required for pkA.

CONCLUSIONS

It appears that Peptide T, a protein kinase A enhancer, produces both symptomatic and functional improvement in patients with a diagnosis of Chronic Fatigue Syndrome. It accomplishes this improvement without changing the underlying viral infection. These patients report increases in vigor and decreases in fatigue compared to placebo. They are assessed as showing increased functional status for activities of daily living. Neuropsychologic testing reveals clinically significant improvements in cognitive and neuromotor function compared to placebo control periods.

All publications hereinabove are hereby incorporated by reference.

While the foregoing invention has been described in some detail for purposes of clarity and understanding, it will be appreciated by one skilled in the art from a reading of this disclosure that various changes in form and detail can be made without departing from the scope of the invention.

What is claimed is:

1. A method of treating chronic fatigue syndrome not associated with an HIV infection comprising administering to a patient with chronic fatigue syndrome a pharmaceutically acceptable carrier with (1) a pharmaceutically effective amount of a linear peptide of formula (I):

$$R^a\text{-Ser-Thr-Thr-Thr-Asn-Tyr-}R^b \qquad (I)$$

wherein $R^a$ is Ala, D-Ala or Cys-Ala-, and
$R^b$ is Thr, Thr-amide, Thy-Cys or Thr-Cys-amide, or an ester or amide derivative of said peptide or a physiologically acceptable salt thereof; or (2) a pharmaceutically effective amount of a linear peptide of formula (II):

$$R^1\text{-}R^2\text{-}R^3R^4\text{-}R^5 \qquad (II)$$

wherein $R^1$ is X-Y or Y wherein Y is Thr-, Ser-, Asn-, Leu-, Ile-, Arg- or Glu-, and X is Cys;
$R^2$ is Thr, Ser or Asp;
$R^3$ is Thr, Ser, Asn, Arg, Gln, Lys or Trp;
$R^4$ is Tyr; and
$R^5$ is Z-X or Z wherein Z is any amino acid and X is Cys, or an ester or amide derivative of said peptide or a physiologically acceptable salt thereof, or (3) a pharmaceutically effective amount of a linear peptide of formula (III):

$$R^x\text{-}R^2\text{-}R^3R^4\text{-}R^y \qquad (III)$$

wherein $R^x$ is Ala-$R^1$, D-Ala-$R^1$ or X-Ala-$R^1$ wherein X, $R^1$, $R^2$, $R^3$, $R^4$ are as defined above, and $R^y$ is Thr-, Thr-amide or Thr-Cys, or an ester or amide derivative of said peptide or a physiologically acceptable salt thereof.

2. The method according to claim 1 wherein the peptide administered is of formula (I):

$$R^a\text{-Ser-Thr-Thr-Thr-Asn-Tyr-}R^b \qquad (I)$$

wherein
$R^a$ is Ala, D-Ala or Cys-Ala-, and $R^b$ is Thr, Thr-amide, Thy-Cys or Thr-Cys-amide, or a derivative of said peptide or a physiologically acceptable salt thereof.

3. The method according to claim 2 wherein the peptide administered is Peptide T (Ala-Ser-Thr-Thr-Thr-Asn-Tyr-Thr) or D-Ala-Ser-Thr-Thr-Thr-Asn-Tyr-Thr-amide.

4. The method according to claim 1 wherein $R^5$ is Thr, Arg or Gly.

5. The method according to claim 1 wherein said derivatives is an ester or an amide derivative.

* * * * *